United States Patent [19]

Matthews et al.

[11] Patent Number: 4,810,800

[45] Date of Patent: Mar. 7, 1989

[54] NOVEL IMIDAZOLE DOPAMINE BETA HYDROXYLASE INHIBITORS

[75] Inventors: Donald P. Matthews; James R. McCarthy, both of West Chester, Ohio; Jeffrey P. Whitten, Zionsville; Robert J. Broersma, Jr., Noblesville, both of Ind.

[73] Assignee: Merrell Dow Pharmaceuticals Inc., Cincinnati, Ohio

[21] Appl. No.: 188,661

[22] Filed: Apr. 29, 1988

Related U.S. Application Data

[63] Continuation of Ser. No. 114,166, Oct. 27, 1987, abandoned, which is a continuation-in-part of Ser. No. 860,263, May 6, 1986, abandoned.

[51] Int. Cl.$^4$ .................. C07D 409/04; C07D 409/06; C07D 401/04; C07D 401/06
[52] U.S. Cl. .................................... 548/336; 544/333; 546/278; 548/203; 548/204; 548/205
[58] Field of Search ................... 544/333; 546/278; 548/203, 204, 205

[56] References Cited

FOREIGN PATENT DOCUMENTS 2650231 4/1978 Fed. Rep. of Germany ...... 548/336

OTHER PUBLICATIONS

Elena Belgodere, et al., *Heterocycles*, 20, 2019–2023 (1983).
*Chemical Abstracts*, 66, 101065t (1967).

*Primary Examiner*—Robert Gerstl
*Attorney, Agent, or Firm*—John J. Kolano

[57] ABSTRACT

1,2-Disubstituted imidazoles useful as antihypertensive agents are described herein. The compounds are obtained from the appropriate 1-substituted imidazole which can be reacted with methyl oxalyl chloride to give the oxalyl derivative or it can be reacted with cyanogen chloride to give the 2-carbonitrile which can then be converted to the other derivatives desired.

9 Claims, No Drawings

NOVEL IMIDAZOLE DOPAMINE BETA HYDROXYLASE INHIBITORS

This is a continuation of application Ser. No. 114,166, filed Oct. 27, 1987, abandoned, which is a continuation-in-part of application Ser. No. 860,263, filed May 6, 1986, abandoned.

The present invention relates to novel derivatives of 1-substituted imidazoles, to the processes and intermediates useful for their preparation, to the pharmaceutical compositions containing said imidazoles, to their dopamine beta-hydroxylase inhibiting pharmacological activity and to their applied use in the treatment of hypertension.

More specifically, this invention relates to novel 1-imidazole derivatives of the formula

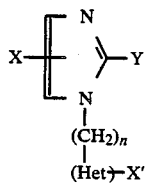

I and the non-toxic pharmaceutically acceptable salts thereof, wherein n is zero or 1–4; X is hydrogen, $C_{1-6}$ lower alkyl, chloro, bromo, phenyl, benzyl, or Z-substituted phenyl or benzyl with Z being $C_{1-6}$ lower alkyl or halogen; Y is $-CH_2NR_1R_2$, $-CONH_2$, $-COCOOR_1$, $-CSNH_2$ or $-C(=NH)NR_1R_2$; $R_1$ and $R_2$ independently represent hydrogen or $C_{1-6}$ lower alkyl; (Het) is a heterocycle of the group consisting of thienyl, furyl, pyridinyl, pyrazolyl, pyrimidinyl, pyrrolyl, thiazolyl and imidazol-2-yl; and X' is hydrogen, halogen or $C_{1-6}$ lower alkyl. The compounds show dopamine beta-hydroxylase inhibiting activity and are useful in the treatment of hypertension.

The "lower alkyl" groups referred to above are straight or branched-chain hydrocarbyl radicals having up to six carbon atoms, preferably methyl, ethyl and propyl; the halogen groups referred to above are illustrated by chloro, fluoro or bromo; in the Z substituted phenyl or benzyl referred to above, those substituents can be at the ortho or meta positions, but preferably they are located at the para-position. The heterocycle terms represented by "Het" in formula I can be exemplified by 2- and 3-thienyl, 2- and 3-furyl; 2-, 3- and 4-pyridinyl; 2-, 4- and 5-pyrimidinyl; 2- and 3-pyrrolyl and their 2,5-dihydro 1H-pyrrolyl analogs; and 3-, 4- and 5-pyrazolyl and its 4,5-dihydro analogs. The heterocyclic moieties may also contain halogeno or lower alkyl substituents at any of their open positions, i.e., X' is hydrogen, halogeno or $C_{1-6}$ lower alkyl. In those instances wherein n is zero, the heterocyclic moiety is attached directly to the nitrogen atom of the imidazole moiety. Otherwise, it is separated by an alkylene bridging moiety having up to four carbon atoms and such groups are illustrated by methylene, ethylene, trimethylene and tetramethylene. Those compounds in which n is 1 (i.e., the bridging group is methylene) are preferred.

The compounds of formula I wherein Y is aminomethyl or amidine are useful in the free base form and in the form of their acid addition salts, both forms being within the purview of this invention. The acid addition salts are simply a more convenient form for use and, in practice, use of the salt amounts to use of the free base.

The acids which can be used include those which produce, when combined with the free base, pharmaceutically acceptable salts, that is, salts whose anions are relatively innocuous to the animal organism in pharmaceutical doses of the salts. In practice, it is convenient to form sulfate, phosphate, methanesulfonate or lactate salts. Others are those derived from mineral acids (e.g., hydrochloric), and organic acids such as acetic acid, citric acid, tartaric acid, ethanesulfonic acid, benzenesulfonic acid, p-toluenesulfonic acid and the like. The acid salts are prepared by standard techniques such as by dissolving the free base in aqueous or aqueous-alcohol solution or other suitable solvents containing the appropriate acid and isolating by evaporating the solution, or by reacting the free base and in an organic solvent in which case the salt separates directly or can be obtained by concentration of the solution.

In the preparation of the compounds of this invention it is quite obvious that the specific compound sought to be prepared will have a bearing on the particular process path to be utilized. Such factors as the specific X, X' and/or Z substituents, the particular alkylene bridge present between the imidazolyl moiety and its attached heterocycle, and ready availability of the starting materials all play a role in choosing the specific path to be followed in the preparation of the compounds of this invention. Those factors are readily appreciated by one of ordinary skill in the art. However, in general, the compounds of this invention may be prepared by standard techniques and processes analogously known in the art.

Specifically, the compounds of the present invention are prepared from an appropriate 2-cyanoimidazole of the formula

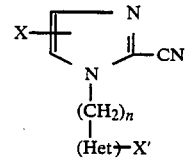

wherein Het, n, X and X' are defined as above. The cyano moiety may readily be converted to its aminomethyl derivatives by standard reduction procedures (i.e., $LiAlH_4$, or $H_2/PtO_2$, or $H_2/Pd/C/HCl$) using well known reducing reagents for this conversion. Alkylation of the aminomethyl moiety ($-CH_2NH_2$) may be effected by use of the Borsch reduction in the presence of the appropriate aldehyde (i.e., reacting RCHO/NaCNBH$_3$ in ethanol at room temperature at pH 4.0–5.0). The imidate ester

(Y is HN=C—OR)

is prepared by reacting the appropriate alcohol with the cyano derivative. The imidate ester

HN=C—OR)

is readily converted to its amidino derivative

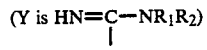
(Y is HN=C—NR$_1$R$_2$)

by reaction with the appropriate amine in acid. Treatment of the amidine

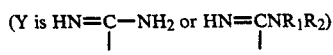
(Y is HN=C—NH$_2$ or HN=CNR$_1$R$_2$)

with H$_2$S in pyridine (with warming) yields the corresponding thioamides (Y is —CSNH$_2$ or —CSNR$_1$R$_2$). Alternatively, the cyano moiety may be treated with H$_2$S in pyridine to yield the desired thioamide (Y is —CSNH$_2$). Acid catalyzed hydrolysis of the nitrile yields the amide (Y is —CONH$_2$).

The cyano starting materials are readily prepared by reacting the imidazole (Id) with cyanogen chloride, in a nitrogen atmosphere, in a solvent, preferably acetonitrile or toluene, at room temperature and then treating the reaction product with a base, preferably triethylamine at below 0° C. temperatures. These procedures are standard and well known in the art and are illustrated below.

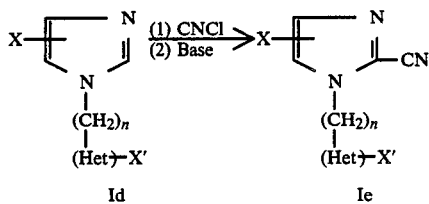

A number of procedures can be used to prepare the imidazole starting materials (Id) shown above. One such approach involves the use of sulfhydryl-substituted imidazoles and, when n is either zero or an alkylene bridge, it is convenient to prepare such compounds by reacting an isothiocyanate derivative (II) with an appropriate acetal (III) to form a reaction product (IV), which is subjected to a cyclization reaction to form the imidazole ring bearing the sulfhydryl substituent (Ia). These reactions are depicted in Reaction Scheme A in which (III) is shown as the methyl acetal although, obviously, the ethyl acetal could also be used.

REACTION SCHEME A

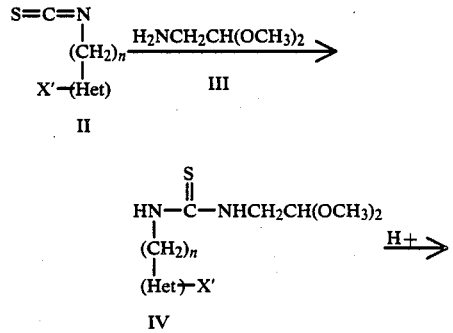

-continued
REACTION SCHEME A

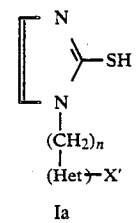

wherein Het, n, and X' are as defined in formula I.

Although it is not shown in the reaction scheme above, the acetal (III) can be substituted at either position on the two-carbon chain by a group X wherein X is alkyl, phenyl, benzyl or substituted phenyl or benzyl and this would give the correspondingly substituted imidazole on cyclization of the thiourea obtained first. In those instances where it is desired to prepare a halogenated derivative, i.e., X in formula I is chloro or bromo, then the thione (Ia) is appropriately protected and the protected compound is halogenated according to procedures well known in the art.

The reaction of the isothiocyanate derivatives (II) with the acetal (III) is a simple condensation reaction, preferably effected by heating the reactants under reflux conditions using inert solvents, e.g., toluene or DMF at 80° C., to form the thiourea (IV) intermediates. These intermediates are subjected to cyclization by treatment with acid, preferably by refluxing the intermediates with aqueous hydrochloric acid in ethanol to produce the desired 1-substituted-2-imidazole bearing a sulfhydryl substituent (Ia). The sulfhydryl moiety can then be chemically removed by catalytic reduction (i.e., desulfurization), preferably utilizing Raney nickel; by oxidation with dilute nitric acid at 80° C. to 90° C. or by other equivalently functional systems.

Alternatively, in those instances wherein n is other than zero, the 1-hetero-2-sulfhydryl-imidazoles (Ic) may be prepared by treating a heteroaldehyde derivative (V) with the aforementioned acetals (III) to form a Schiff base which is reduced to form an intermediate (VI) which is subjected to a cyclization reaction by treatment with aqueous HCl in ethanol in the presence of an alkali metal isothiocyanate, preferably KSCN. These reactions may be depicted by the following reaction scheme.

REACTION SCHEME B

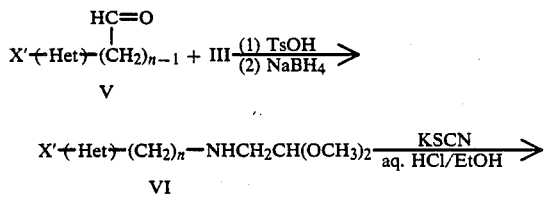

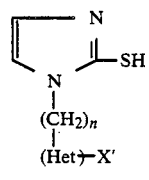

wherein (Het) and X' are as previously defined and n is defined as above.

An alternate method for preparing the intermediate compounds of formula Id is by reacting a halo derivative of an appropriate heterocycle with an X-substituted imidazole to form a X'-(Het)-(CH$_2$)$_n$-substituted-X-substituted-imidazole. In one illustration of this type reaction the imidazole is first acylated and then the N-acylated imidazole is treated with a halo derivative of an approopriate heterocyclic to form an intermediate N'-acylated-N$^3$-imidazolium cation which is hydrolyzed to form the appropriately X-substituted analogs of Id. In another illustration the alkali metal derivatives of an X-substituted imidazole may be reacted with a halo derivative of an appropriate heterocycle to produce the desired 1-(2-heterocycle)-X-substituted imidazole; the reaction being effected according to standard and well known conditions. These reactions are depicted by the following reaction scheme.

REACTION SCHEME C

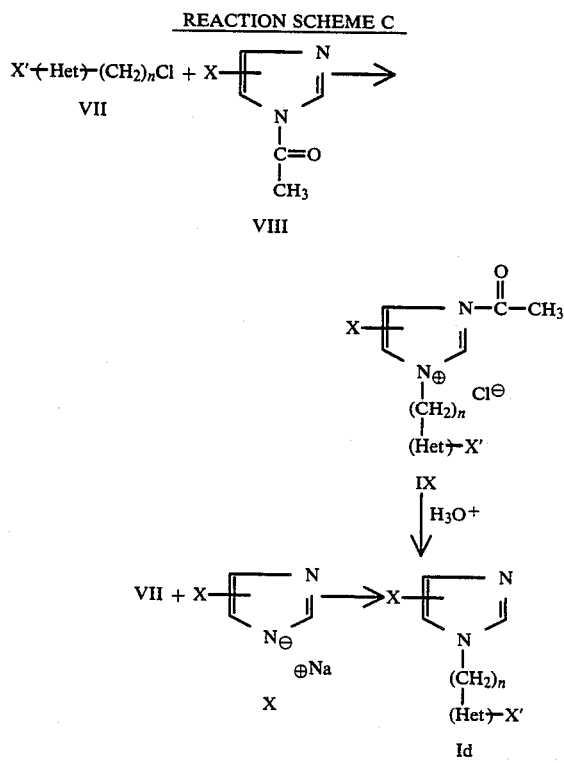

wherein the (Het), X', X and n moieties are as previously defined.

Useful references for some of the foregoing reactions are *J. Med. Chem.* 28, 1405–1413 (1985); *J. Med. Chem.* 10, 1409 (1985); *J. Med. Chem.* 18, 833 (1975) and *Chem. Rev.* 390 (1944).

The following examples merely illustrate the various techniques and procedures utilized for the preparation of the compounds of this invention; it being understood that they are not meant to limit the scope of the compounds defined by this invention.

EXAMPLE 1

1,3-Dihydro-1-(2-thienylmethyl)-2H-imidazole-2-thione

A mixture of 33.6 g (0.3 mol) thiophene-2-carboxaldehyde, 39.9 g (0.3 mol) aminoacetaldehyde diethyl acetal, 0.3 g 4-toluenesulfonic acid (TsOH) and 200 ml ethanol is placed in a 500 ml flask and heated to reflux. After 2 hours, the reaction is concentrated and the residue dissolved in 250 ml ethanol. Solid NaBH$_4$ (12.5 g, 0.33 mol) is added in small portions. The reaction is refluxed for 1½ hours, cooled to room temperature and poured into cold water. The product is extracted into CH$_2$Cl$_2$ (2×250 ml). After drying (Na$_2$SO$_4$) and concentration, 66.7 g crude product is obtained as a pale yellow oil. 22.9 g (0.1 mol) of the crude amine is placed in a 500 ml flask along with 11.7 g (0.12 mol) KSCN, 150 ml ethanol, 40 ml water and 15 ml concentrated hydrochloric acid. After refluxing for 5 hours, the reaction is poured onto 1 liter of ice water. The white crystals are collected and dried to give 12.0 g (61%) product, mp 128°–130° C. (EtOH).

EXAMPLE 2

1,3-Dihydro-1-(1-methylpyrrol-2-ylmethyl)-2H-imidazole-2-thione

Reflux a mixture of 10.0 g (0.1 mol) 1-methyl-2-pyrrolecarboxaldehyde, 13.1 g (0.1 mol) aminoacetaldehyde diethylacetal, 0.1 g TsOH.H$_2$O and 200 ml ethanol for 2 hours. Cool and concentrate the resulting mixture to obtain a tan oil. Dissolve the residue in 200 ml ethanol and slowly add 4.2 g (0.11 mol) solid NaBH$_4$. After addition is completed, reflux the reaction mixture for 2 hours, pour the cooled reaction mixture into 1 liter of water. Extract the product into CH$_2$Cl$_2$ (2×200 ml), dry (Na$_2$SO$_4$) and concentrate to obtain 24.2 g of crude acetal derivative. Mix the acetal derivative (22.6 g, 0.01 mol) with 11.6 g (0.12 mol) KSCN, 150 ml ethanol, 40 ml H$_2$O and 15 ml concentrated hydrochloric acid, reflux the mixture for 6 hours and pour the resulting mixture into 1 liter of ice water. Collect and dry the resulting crystals.

EXAMPLE 3

1,3-Dihydro-1-(4-pyrazolylmethyl)-2H-imidazole-2-thione

Under reflux conditions, heat a mixture of 9 g (0.14 mol) 4-pyrazolylcarboxaldehyde, 0.1 g TsOH, 18.6 g (0.14 mol) aminoacetaldehyde diethylacetal and 150 ml ethanol for 1½ hours. Cool and concentrate reaction mixture, redissolve residue in 200 ml ethanol. Slowly add 5.7 g (0.15 mol) solid NaBH$_4$ and reflux the resulting mixture for 3 hours, pour the mixture into water. Extract the intermediate aminoacetal derivative into CH$_2$Cl$_2$ (2×150 ml). Dry (over Na$_2$SO$_4$) and concentrate the resulting mixture to give 32.1 g of a tan residue. Dissolve the entire residue in 150 ml ethanol and further add 15.5 g (0.16 mol) KSCN, 40 ml H$_2$O and 15 ml concentrated HCl. Reflux the mixture for 5 hours, allow the mixture to cool and pour into 1 liter of ice water and neutralize with dilute NaOH. Collect and dry the resulting crystals.

EXAMPLE 4

1,3-Dihydro-1-(4-pyrimidinylmethyl)-2H-imidazole-2-thione

A mixture of 10.8 g (0.1 mol) 4-pyrimidinecarboxaldehyde, 13.1 g (0.1 mol) aminoacetaldehyde diethylacetal, 0.1 g TsOH and 300 ml ethanol is placed in a 500 ml round bottomed flask. The reaction is refluxed for 2 hours then concentrated to give the crude imine. The imine is dissolved in 250 ml ethanol and 3.8 (0.1 mol) solid NaBH$_4$ added slowly. After the addition is completed, the mixture is refluxed 2 hours. The reaction is diluted with H₂O to a total volume of 1 liter and the amine derivative extracted into CH₂Cl₂ (2×250 ml). After drying (Na₂SO₄) and concentration, the amine is obtained as an orange oil. Without further purification, the amine is dissolved in 200 ml ethanol and 11.6 g (0.12 mol) KSCN, 40 ml water and 15 ml concentrated hydrochloric acid added. The reaction is gently refluxed for 6 hours, cooled and poured onto ice. The desired product, as a crystalline solid, is collected and dried in a vacuum oven.

EXAMPLE 5

1,3-Dihydro-1-(2-(5-methylimidazolyl)methyl)-2H-imidazole-2-thione

A mixture of 11.0 g (0.1 mol) 4(5)-methyl-2-imidazolecarboxaldehyde, 13.3 g (0.1 mol) aminoacetaldehyde diethylacetal, 0.2 g TsOH and 200 ml ethanol is heated to reflux. After 1 hour, the reaction is cooled and concentrated. The residue is dissolved in 200 ml ethanol and 3.8 g (0.1 mol), solid NaBH₄ added in small portions. The reaction is then refluxed for 2 hours, poured onto 1.2 liters H₂O and the product extracted into CH₂Cl₂ (2×200 ml). The CH₂Cl₂ solution is dried (Na₂SO₄) and concentrated to give a tan oil. The oil is dissolved in 200 ml ethanol and 11.6 g (0.12 mol) KSCN, 40 ml H₂O and 15 ml concentrated hydochloric acid added. The reaction is refluxed for 6 hours. After cooling, the reaction is poured onto 1 liter of ice. The product, tan crystals, is collected by vacuum filtration and dried.

EXAMPLE 6

1,3-Dihydro-1-(2-furanylmethyl)-2H-imidazole-2-thione

A 500 ml flask is charged with 38.4 g (0.4 mol) furan-2-carboxaldehyde, 53.2 g (0.4 mol) aminoacetaldehyde diethylacetal and 100 ml ethanol. The solution is refluxed for 1½ hours then concentrated under vacuum to give an orange oil. This oil is dissolved in 150 ml ethanol and 17 g (0.45 mol) NaBH₄ is added slowly. This mixture is refluxed 1½ hours, cooled and diluted with water. A little glacial acetic acid is added to destroy the excess NaBH₄. The product is extracted into EtOAc (2×300 ml). After drying (NaSO₄) and concentration, 70.3 g amino derivative is obtained; 21.3 (0.1 mol) amino derivative is placed in a 500 ml flask and 11.7 g (0.12 mol) KSCN, 150 ml ethanol, 40 ml water and 15 ml concentrated hydrochloric acid is added. The reaction is refluxed for 5 hours. The cooled reaction is diluted with water and the product extracted into EtOAc. Drying (Na₂SO₄) and concentration gives 14.7 g crude product. Purification by flash chromotography (4% MeOH/CH₂Cl₂) yields 4.75 (26%) desired product mp 105.5°–108° C. (EtOAc).

EXAMPLE 7

1,3-Dihydro-1-(2-thienylmethyl)-2H-imidazole-2-thione

Under a blanket of nitrogen, 11.3 g (0.1 mol) 2-aminomethylthiophene is added to 19.6 g (0.11 mol) 1,1'-thiocarbonyldiimidazole in 200 ml anhydrous toluene at 0° C. The reaction is held at 0° C. for 4 hours. Then 10.5 g (0.1 mol) aminoacetaldehyde dimethyl acetal is added and the reaction is warmed at 80° C. for 2 hours. The toluene is removed and the residue dissolved in 100 ml ethanol, 15 ml water and 15 ml concentrated HCl. The mixture is refluxed 5 hours, cooled and poured onto 1 liter of ice. After recrystallization (1/1 EtOH/H₂O) the desired product is obtained as white shiny crystals, mp 128°–130° C.

EXAMPLE 8

1,3-Dihydro-1-(4-pyridyl)-2H-imidazole-2-thione

Under a blanket of nitrogen, 14.1 g (0.15 mol) 4-aminopyridine is added to 28.5 g (0.16 mol) 1,1'-thiocarbonyldiimidazole in 300 ml anhydrous DMF at 0° C. The reaction is held at 0° C. for 4 hours. To the 4-isothiocyanatopyridine formed 15.8 g (0.15 mol) aminoacetaldehyde dimethyl acetal is added and the reaction is warmed at 80° C. for 24 hours. The reaction is poured into water and extracted with ethyl acetate providing a dark residue on evaporation. This material is dissolved in 200 ml ethanol, 20 ml water and 20 ml concentrated hydrochloric acid. The mixture is refluxed for 5 hours, cooled and poured onto 1 liter of ice. After purification, crystalline product is obtained as a tan solid.

EXAMPLE 9

1,3-Dihydro-1-(2-thienyl)-2H-imidazole-2-thione

A mixture of 2-isothiocyanatothiophene (16.9 g, 0.12 mol), and aminoacetaldehyde dimethyl acetal (12.6 g, 0.12 mol) in 200 ml toluene is refluxed for 2 hours. After removal of the toluene, the residue is dissolved in 200 ml ethanol and 45 ml conc. HCl added. After the reaction is refluxed for 5 hours, it is poured onto ice. The product is collected and purified by recrystallization.

In a similar manner, by following the generic teachings related to Reaction Schemes A to C and by substantially following the procedures of the foregoing examples, there may be prepared the following 1,3-dihydro-2H-imidazole-2-thiones:

5-chloro-1-(2-thienylmethyl)-1,3-dihydro-2H-imidazole-2-thione,
5-bromo-1-(2-thienylmethyl)-1,3-dihydro-2H-imidazole-2-thione,
5-methyl-1-(2-thienylmethyl)-1,3-dihydro-2H-imidazole-2-thione,
4-phenyl-1-(2-thienylmethyl)-1,3-dihydro-2H-imidazole-2-thione,
5-benzyl-1-(2-thienylmethyl)-1,3-dihydro-2H-imidazole-2-thione, and their 1-[2-(2-thienyl)ethyl], 1-[3-(2-thienyl)propyl], 1-[4-(2-thienyl)butyl] and 1-(2-thienyl)homologs.

Similarly, the corresponding analogs of the foregoing may be prepared for the corresponding 1-position pyrazolyl, furyl, pyrimidinyl, pyrrolyl and imidazolyl substituted 1,3-dihydro-2H-imidazole-2-thiones.

EXAMPLE 10

1,3-Dihydro-1-[3-(2-thienyl)propyl]-2H-imidazole-2-thione

A mixture was prepared from 20.8 g of 2-[2-(4-toluenesulfonyloxy)ethyl]thiophene, 5.4 g of sodium cyanide and 175 ml of dimethylsulfoxide and this mixture was heated to 90° C. The mixture was quenched by pouring it into saturated aqueous ammonium chloride solution and the resulting solution was extracted into ethyl acetate. The ethyl acetate solution was dried over sodium sulfate and the solvent was evaporated under reduced pressure to give crude 2-thiophenepropionitrile. This product was mixed with 175 ml of 1M diborane in tetrahydrofuran and allowed to stir at room temperature. The reaction was quenched in ethanol and methanolic hydrogen chloride was added. The white solid which formed was separated by filtration, washed with ether and dried in a vacuum oven to give 3-(2-thienyl)propylamine hydrochloride melting at about 197°–198° C.

A solution of 4.1 g of 3-(2-thienyl)propylamine (obtained from the hydrochloride by standard procedures) in about 100 ml of dimethylformamide was cooled to 0° C. and 5.7 g of solid 1,1'-thiocarbonyldiimidazole was added. The mixture was allowed to warm slowly to room temperature and then stirred for 16 hours. It was then poured into water and the resulting aqueous mixture was extracted with three portions of ethyl acetate. Saturated sodium chloride solution was added to break up any emulsion. The resulting ethyl acetate solution was washed with water, dried over sodium sulfate and then concentrated. The crude product obtained was mixed with 3.0 g of aminoacetaldehyde dimethyl acetal in 80 ml of dimethylformamide and heated at 80° C. for 3 hours. The mixture was then cooled to room temperature and the solvent was removed under reduced pressure. The residue was dissolved in ethanol and 2.5N hydrochloric acid was added to hydrolyze the acetal. The mixture was heated at reflux for 2 hours and then cooled to room temperature and poured into 500 g of ice. The resulting mixture was then heated to remove any remaining ethanol but no solid formed in the residual mixture which was then extracted with three portions of ethyl acetate. The ethyl acetate extracts were combined and dried over sodium sulfate and the solvent was evaporated to give a residual tan oil. This oil crystallized on standing and was recrystallized from toluene to give 1,3-dihydro-1-[3-(2-thienyl)propyl-2H-imidazole-2-thione melting at about 94°–96.5° C.

EXAMPLE 11

1,3-Dihydro-1-[2-(2-thienyl)ethyl]-2H-imidazole-2-thione

To 4000 ml of 1M diborane/tetrahydrofuran there was added 170 g of 2-thiopheneacetonitrile over a period of 30 minutes. The reaction temperature gradually warmed to 47° C. during the addition and the mixture was then allowed to cool to room temperature and stand and stir for 5 days. The colorless reaction was quenched by the addition of 800 ml of ethanol followed by 300 ml of saturated methanolic hydrogen chloride until the mixture became acidic. The solid which precipitated from the solution was collected by filtration, washed with ether and then dried in a vacuum oven at 50° C. to give 2-(2-thienyl)ethylamine hydrochloride melting at about 198°–200° C.

2-(2-Thienyl)ethylamine (91 g, obtained by partitioning the hydrochloride salt between ethyl acetate and ice cold 2N sodium hydroxide, washing the organic layer with brine, drying with sodium sulfate and evaporating the solvent in vacuo to a colorless oil) in 500 ml of dimethylformamide was added all at once to an ice cooled solution of 142 g of 90% 1,1'-thiocarbonyldiimidazole in dimethylformamide. The mixture was stirred for 16 hours at room temperature and then poured into 4000 ml of brine. The resulting solution was extracted with three portions of ethyl acetate and the combined organic layers were washed with water and dried over sodium sulfate and the solvent was evaporated to leave a residual oil which was the isothiocyanate corresponding to the starting amine. To a solution of 194 g of this crude isothiocyanate in 300 ml of dimethylformamide there was added 75 g of aminoacetaldehyde dimethyl acetal. The reaction warmed to 70° C. and was further heated at 80° C. for 2.5 hours. After the mixture was cooled to room temperature, the dimethylformamide was removed by Kugelrohr distillation. The residual orange oil was mixed with 500 ml of 10% aqueous hydrochloric acid and 300 ml of ethanol and heated at a gentle reflux for 2 hours. The resulting solution was cooled and poured onto 3 liters of ice with stirring. Crystallization was induced by the addition of a seed crystal and the solid which formed was separated by filtration and dried in a vacuum oven at 50° C. It was then recrystallized from toluene to give 1,3-dihydro-1-[2-(2-thienyl)ethyl]-2H-imidazole-2-thione melting at about 131°–134° C.

EXAMPLE 12

If the appropriate alcohol is used as the starting material and it is reacted with 4-toluenesulfonyl chloride to give the corresponding sulfonate ester which is then further reacted according to the procedure described in Example 10, or the appropriate nitrile is used as the starting material and it is further reacted according to the procedures described in Examples 10 or 11, the following compounds are obtained:

1,3-Dihydro-1-[2-(5-chloro-2-thienyl)ethyl]-2H-imidazole-2-thione.

1,3-Dihydro-1-[2-(5-bromo-2-thienyl)ethyl]-2H-imidazole-2-thione.

1,3-Dihydro-1-[2-(5-methyl-3-thienyl)ethyl]-2H-imidazole-2-thione.

1,3-Dihydro-1-[2-(2-methyl-3-thienyl)ethyl]-2H-imidazole-2-thione.

1,3-Dihydro-1-[2-(5-chloro-2-furyl)ethyl]-2H-imidazole-2-thione.

1,3-Dihydro-1-[2-(5-bromo-2-furyl)ethyl]-2H-imidazole-2-thione.

1,3-Dihydro-1-[2-(5-methyl-2-furyl)ethyl]-2H-imidazole-2-thione.

1,3-Dihydro-1-[3-(5-methyl-2-furyl)propyl]-2H-imidazole-2-thione.

1,3-Dihydro-1-[4-(5-methyl-2-thienyl)butyl]-2H-imidazole-2-thione.

1,3-Dihydro-1-[2-(5-chloro-1-methyl-1H-imidazol-2-yl)ethyl]-2H-imidazole-2-thione.

1,3-Dihydro-1-[2-(1H-pyrazol-3-yl)ethyl]-2H-imidazole-2-thione.

1,3-Dihydro-1-[2-(4-bromo-1H-pyrrol-2-yl)ethyl]-2H-imidazole-2-thione.

1,3-Dihydro-1-[2-(4-chloro-1H-pyrrol-2-yl)ethyl]-2H-imidazole-2-thione.

1,3-Dihydro-1-[2-(6-chloro-2-pyridinyl)ethyl]-2H-imidazole-2-thione.

1,3-Dihydro-1-[2-(4-methyl-2-pyridinyl)ethyl]-2H-imidazole-2-thione.

1,3-Dihydro-1-[2-(5-methyl-2-pyridinyl)ethyl]-2H-imidazole-2-thione.

EXAMPLE 13

1-(2-Thienyl)-1H-imidazole

Under nitrogen, solid imidazole (34 g, 0.5 mol) is added cautiously to a slurry of 20.9 g (0.55 mol) 50% NaH dispersion in 500 ml dry DMF. After hydrogen evolution ceases, 115 g (0.55 mol) 2-iodothiophene in 100 ml DMF is added. The reaction is heated at 150° C. for 18 hours. After cooling, the reaction is diluted with 2 liters of water and the product extracted into EtOAc (2×400 ml). After drying, (Na$_2$SO$_4$) the solvent is removed to give crude 1-(2-thienyl)imidazole. The product is purified by vacuum distillation.

EXAMPLE 14

1-(3-Thienylmethyl)-1H-imidazole

In a 3 neck, round-bottomed flask reflux a mixture of 11.6 g (0.17 mol) imidazole, 30 g (0.17 mol) 3-bromomethylthiophene, 46 g (0.33 mol) K$_2$CO$_3$ and 400 ml dry acetone. After refluxing for 4 hours filter the reaction mixture and wash the inorganic solids with acetone. Remove the acetone under vacuum and partition the residue betwen H$_2$O/EtOAc. Wash the EtOAc layer several times with H$_2$O, dry (Na$_2$SO$_4$) and concentrate the washed material to obtain a pale yellow oil.

EXAMPLE 15

1-(4-Pyridyl)-1H-imidazole

An ethanolic solution of 5.9 g (0.028 mol) 1,3-dihydro-1-(4-pyridyl)-2H-imidazole-2-thione prepared in Example 8 is charged with 23.0 g Raney nickel and 10 ml concentrated ammonium hydroxide. The black slurry is refluxed for 2 hours, then filtered to remove the nickel catalyst. The ethanol is removed under vacuum and the product is extracted into CH$_2$Cl$_2$ (2×100 ml). Drying (NaSO$_4$) and concentration gives the 1-(4-pyridyl)-1H-imidazole.

In a similar manner, the 2-thiones preparable by the procedures of Examples 1-12 are converted to their corresponding desulfurized product by following the procedure of this example.

EXAMPLE 16

2-Cyano-1-(3-thienylmethyl)-1H-imidazole

In a 250 ml, 4-neck flask equipped with a nitrogen bubbler, gas inlet tube, thermometer and septum, add 100 ml acetonitrile and bubble cyanogen chloride (15 g, 0.24 mol) into the acetonitrile. Cool the solution in an ice bath and add 8.2 (0.05 mol) 1-(3-thienylmethyl)-1H-imidazole. After the colorless solution turns yellow-orange and about 1 hour after an orange precipitate forms, cool the slurry to −20° C., slowly add 42 ml (0.3 mol) of triethylamine, holding the temperature below 0° C. After 1 hour at room temperature, pour the reaction onto 600 ml saturated NaHCO$_3$ and extract with ether (3×150 ml). Dry and combine organic layers to obtain tan oil. The oil is purified via Kugelrohr distillation to obtain a colorless oil.

In a similar manner, by treating the 1-substituted-4X (or 5X)-1H-imidazole product of Example 15 according to the procedures of this example, there may be prepared the corresponding 2-cyano derivatives.

EXAMPLE 17

2-Cyano-1-(2-thienylmethyl)-1H-imidazole

A solution of 20 g of cyanogen chloride in 400 ml of acetonitrile was prepared and then cooled in an ice bath. 1-(2-Thienylmethyl)-1H-imidazole (21.4 g) was added and, after about an hour, the mixture was cooled to −20° C. and 56 ml of triethylamine was added slowly while the temperature was maintained below 0° C. The reaction was quenched with aqueous saturated sodium bicarbonate solution and diluted with water. The mixture was extracted three times with ether and the combined ether extracts were dried over sodium sulfate and concentrated to give a brown oil. This oil was first purified by vacuum distillation on the Kugelrohr and the resulting crude product was then flash chromatographed on silica gel using 5% ethyl acetate/chloroform. The tan oil thus obtained solidified and was recrystallized from a mixture of cyclohexane and toluene to give 2-cyano-1-(2-thienylmethyl)-1H-imidazole melting at about 64°–65° C.

EXAMPLE 18

Methyl α-oxo-1-(2-thienylmethyl)-1H-imidazole-2-acetate

A solution of 1-(2-thienylmethyl)imidazole (4 g, 0.024 mol) in 100 ml CH$_3$CN was charged with 3.0 g methyl oxalyl chloride. The solution was stirred for 1 hour and then 4.1 ml (0.03 mols) Et$_3$N was added. The color changed and a white precipitate was formed. (TLC (60% EtOAc/hex) showed mainly one spot.) The mixture was diluted with H$_2$O and the product extracted into EtOAc (2×150 ml). After drying (Na$_2$SO$_4$) and concentration, 6.7 g of a brown oil was obtained. Flash chromatography (60% ethyl acetate/hexane) gives 6.2 of the desired product as an orange-yellow oil.

In a similar manner, by treating the 1-substituted 4X (or 5X)-1H-imidazole products prepared according to the procedures of Example 15, the analogous alpha keto esters may be prepared, which compounds may also be converted to the analogous alpha keto acids by standard procedures.

EXAMPLE 19

2-Aminomethyl-1-(3-furylmethyl)-1H-imidazole

Place 4.0 g (0.021 mol) 2-cyano-1-(3-furylmethyl)-1H-imidazole, 20 ml ethanolic HCl, 20 ml ethanol and 1 g 10% Pd/C in a Parr hydrogenator with an initial pressure of 52 psi. After 18 hours remove the reaction mixture from the Parr hydrogenator, add 20 ml H$_2$O, remove the catalyst by filtration, concentrate the filtrate to obtain an off-white solid which is recrystallized from ethanol containing a little concentrated HCl to give the desired product as a white solid.

In a similar manner, the 2-cyano derivatives prepared according to procedures of Example 16 may be converted to their 2-aminomethyl derivatives by following the procedure of this example.

EXAMPLE 20

Ethyl 1-(3-thienylmethyl)-1H-imidazole-2-carboximidate

Under a blanket of nitrogen, mechanically stir a solution of 2-cyano-1-(3-thienylmethyl)-1H-imidazole (10 g. 0.052 mol), absolute ethanol (2.4 g, 0.052 mol) and 500 ml chloroform. The solution is cooled to −10° C. and anhydrous HCl is sparged into the reaction for 1 hour as the temperature is held below 0° C. Stir the reaction for 1 hour at 0° C. under dry nitrogen. The excess hydrogen chloride is removed by bubbling dry nitrogen through the reaction. Shake the chloroform solution with cold saturated sodium bicarbonate. After drying (NaSO$_4$) and concentration, the imidate is obtained as a colorless oil that rapidly crystallized.

In a similar manner, the 2-cyano derivatives prepared according to the procedures of Example 16 may be converted to their analogous imino esters by following the procedure of this example.

EXAMPLE 21

1-(3-Thienylmethyl)-2-thiocarbamyl-1H-imidazole

Hydrogen sulfide is sparged into a solution of 3.0 g (0.015 mol) of the amidine of Example 24 in 20 ml pyridine for 5 minutes. The reaction is warmed at 50° C. for 8 hours. After cooling, the majority of the pyridine is removed under vacuum. The residue is mixed with 200 ml cold water. The yellow solid is collected and dried.

EXAMPLE 22

1-(3-Thienylmethyl)-2-carbamyl-1H-imidazole

A mixture of 5.0 g (0.026 mol) of the nitrile of Example 16 and 120 ml concentrated hydrochloric acid is placed in a 500 ml round bottomed flask. A small amount of ethanol is added to aid in solubility of the nitrile. The reaction is refluxed for 8 hours and then the ethanol is distilled away. The white crystals are collected and dried.

In a similar manner, the 2-cyano derivatives preparable according to the procedures of Example 16 may be converted to their analogous 2-carbamyl derivatives by following the procedures of this example.

EXAMPLE 23

1,3-Dihydro-1-(2-thiazolylmethyl)-2H-imidazole-2-thione

In a 500 ml round bottom blask is placed 6 g (0.053 mol) 2-thiazolecarboxaldehyde, 7.0 g (0.053 mol) aminoacetaldehyde diethylacetal, 0.1 g TsOH and 150 ml ethanol. The reaction is refluxed 2 hours, cooled and concentrated. The residue is redissolved in 200 ml ethanol and 2.3 g (0.06 mol) NaBH$_4$ added. The reaction is refluxed 4 hours then poured onto 500 ml water. The amino derivative is extracted into CH$_2$Cl$_2$ (2×100 ml), dried (Na$_2$SO$_4$) and concentrated to give an orange oil. The entire product is dissolved in 200 ml ethanol and 5.1 g (0.053 mol) KSCN, 30 ml water and 8 ml concentrated HCl added. The reaction is refluxed for 6 hours, cooled and then poured onto 1 liter ice water. The tan solid is collected and dried.

EXAMPLE 24

1-(3-Thienylmethyl)-1H-imidazole-2-carboximidamide hydrochloride

An ethanolic solution of 12 g (0.051 mol) imino ester of Example 20 is treated with 4.0 g (0.074 mol) NH$_4$Cl in 20 ml ethanol. The solution was stirred at room temperature for 7 hours, then concentrated to give a white solid. Recrystallization (ethanol) gives the amidine hydrochloride salt as colorless crystals.

In a similar manner, the 2-imino esters prepared by the procedures of Example 20 (or their N-alkyl derivatives) may be converted to the analogous amidine derivatives by following the procedure of this example.

EXAMPLE 25

2-Aminomethyl-1-(2-thienylmethyl)-1H-imidazole 1.9 Grams of lithium aluminum hydride was added to about 50 ml of dry tetrahydrofuran. Then 1.3 ml of sulfuric acid was added by means of a syringe with cooling. The resulting slurry was stirred at room temperature for 1 hour and then a tetrahydrofuran solution of 3.0 g of 2-cyano-1-(2-thienylmethyl)-1H-imidazole was added and the mixture was stirred for 16 hours. The reaction mixture was quenched with 1.9 ml of water, 1.9 ml of 15% aqueous sodium hydroxide solution, and 5.7 ml of water. The mixture was then filtered and the solid was washed with ethyl acetate. The filtrate was then partitioned between water and ethyl acetate. The ethyl acetate layer was separated, dried over sodium sulfate and concentrated to give a yellow oil. A solution of 0.7 g of this oil in 300 ml of ether was prepared and a solution of 3.6 g of 4-toluenesulfonic acid in ethanol was added. The solid which formed was separated by filtration and dried to give 2-aminomethyl-1-(2-thienylmethyl)-1H-imidazole 4-toluenesulfonate melting at about 129°–131° C.

EXAMPLE 26

1-(2-Thienylmethyl)-2-thiocarbamyl-1H-imidazole

Hydrogen sulfide gas was bubbled into 100 ml of cooled pyridine to give a saturated solution. Then, 5.0 g of 2-cyano-1-(2-thienylmethyl)-1H-imidazole was added and the mixture was heated to reflux. The reaction mixture was then cooled to room temperature and poured into 1000 ml of water. The yellow solid which formed was separated by filtration to give 1-(2-thienylmethyl)-2-thiocarbamyl-1H-imidazole melting at about 152°–153° C.

The various cyano compounds described in Example 16 are converted to the corresponding thiocarbamyl compounds in a similar way.

EXAMPLE 27

1-(2-Thienylmethyl)-2-carbamyl-1H-imidazole

A mixture of 2.4 g of 2-cyano-1-(2-thienylmethyl)-1H-imidazole in about 20 ml of 5N hydrochloric acid was heated to reflux for 3 hours and then cooled to room temperature. A brown oil settled to the bottom of the reaction mixture. The oil was crystallized from ethanol to give 1-(2-thienylmethyl)-2-carbamyl-1H-imidazole melting at about 152'–154° C.

EXAMPLE 28

1-(2-Thienylmethyl)-1H-imidazole-2-carboximidamide

A mixture was prepared from 7.6 g of 2-cyano-1-(2-thienylmethyl)-1H-imidazole, 300 ml of methanol and 100 mg of sodium. This gave a methanol solution of methyl 1-(2-thienylmethyl)-1H-imidazole-2-carboximidate which was mixed with 6.9 g of ammonium chloride. The resulting mixture was flash chromatographed (chloroform:methanol:ammonium hydroxide 56:7:1) to give a pale tan oil which crystallized on drying under vacuum. A portion of this solid was dissolved in hot ethanol and an ethanolic solution of hydrogen chloride was added. Crystals formed in the solution slowly. The solid which thus formed was separated by filtration to give 1-(2-thienylmethyl)-1H-imidazle-2-carboximidamide dihydrochloride melting at above 245°–248° C.

EXAMPLE 29

Methyl α-oxo-1-(2-thienylmethyl)-1H-imidazole-2-acetate

A solution of 3.0 g of 1-(2-thienylmethyl)-1H-imidazole in 100 ml of acetonitrile was charged with 3.0 g of methyl oxalyl chloride and the resulting mixture was stirred for 1 hour. Then 4.1 ml of triethylamine was added. The color changed and a white precipitate formed. The mixture was diluted with water and then extracted with two portions of ethyl acetate. The ethyl acetate solution was dried over sodium sulfate and concentrated to give a brown oil. This oil was flash chromatographed to give an orange-yellow oil. This new oil solidified and was recrystallized from hexane to give methyl α-oxo-1-(2-thienylmethyl)-1H-imidazole-2-acetate melting at about 72.5°–74.5° C.

The compounds of this invention exhibit valuable in vitro and in vivo pharmacological effect in that they are dopamine beta-hydroxylase (DBH) inhibitors and thus would be valuable therapeutic agents useful in the treatment of hypertension.

The DBH inhibitory properties of the compounds of this invention can readily be determined in vitro by standard and well known procedures for assaying conversion of tyramine to octopamine in the presence of dopamine beta-hydroxylase. Enzymatic oxygenation by DBH is determined in aqueous solution in the presence of molecular oxygen, an electron donor such as ascorbate, and the necessary cofactors for the enzyme at pH of 5 and a temperature of 20°–40° C., preferably 37° C. The test compound is added at the desired concentration, and the system is incubated. Activity is measured by measuring the oxygen uptake using a polarographic electrode and an oxygen monitor by the method of S. May, et al., *J. Biol. Chem.* 256, 2258 (1981). Inhibition is given in molar concentration of compound at which DBH activity was halved ($IC_{50}$) when the test compounds were tested according to the above described procedure. The $IC_{50}$ (expressed in micromolar units) data of some of the compounds of this invention are expressed in Table I.

The compounds of this invention may also be tested for their in vivo DBH inhibiting property according to the procedure of Felice, Felice and Kessinger, *J. Neurochem.*, 31, 1461–1465 (1978) wherein the effects on peripheral dopamine and norepinephrine levels are determined. In this test spontaneously hypertensive rats are dosed (i.p.) at 50 mg per kilogram of body weight and sacrificed six hours later. Average results, expressed in micrograms of dopamine (DA) per gram of heart tissue are determined with the difference between the control and the treated rats being the in vivo (DBH) inhibitory effect of the test compound.

The ability of the compounds of this invention to lower blood pressure can be determined in vivo using spontaneously hypertensive rats (SHR'S) according to standard and well known procedures. The test compound is administered intraperitoneally (ip) to rats and the blood pressure monitored continuously. Snce DBH is a major enzyme in the synthetic pathway of the catecholamines, it would be expected that the presence of an inhibitor would act to decrease the amount of catecholamines produced, and thereby have an antihypertensive effect. The results of the testing for this antihypertensive effect are shown in Table I (MBP is mean blood pressure).

TABLE I

Inhibition of DBH In Vitro and
In Vivo at 50 mg/kg, IP, 6 Hours Post Dose in SHR's*

| Compound | $IC_{50}$ (μM) | Max Change MBP (mmHg) |
|---|---|---|
| 1 | 12.8 | −41 ± 14[a] |
| 2 | 4.7 | −25 ± 12[a] |

*Spontaneously Hypertensive Rats.
[a]Mean Difference ± Standard Deviation.
Compound 1 - 2-Aminomethyl-1-(2-thienylmethyl)-1H—imidazole
Compound 2 - 1-(2-Thienylmethyl)-2-thiocarbamyl-1H—imidazole Based on the foregoing test results, as well as by comparison with similar test results for compounds known to be useful, the compounds of this invention exert their DBH inhibiting effects (i.e., their $IC_{50}$ effects) at from 1 to 2000 micromolar concentrations and are expected to exhibit end-use antihypertensive activity at doses of about 10 mg to 1000 mg per kilogram of body weight.

As is true in most large classes of compounds suitable for use as chemotherapeutic applications, certain subgeneric groups and certain specific compounds will exhibit properties which render them more preferable than the entire class. In this instance those compounds of formula I wherein X is hydrogen are preferred; compounds wherein Y is —$CH_2NH_2$ or —$CSNH_2$ are also preferred; compounds wherein n is 1 are preferred and compounds wherein the heterocycle is 2- or 3-thiophene or furan are preferred. Specifically preferred compounds are:

2-Aminomethyl-1-(2-thienylmethyl)-1H-imidazole;
1-(2-Thienylmethyl)-2-thiocarbamyl-1H-imidazole;
Methyl α-oxo-1-(2-thienylmethyl)-1H-imidazole-2-acetate;
1-(2-Thienylmethyl)-1H-imidazole-2-carboximidamide dihydrochloride.

As stated above, the compounds of this invention are useful in the treatment of hypertension. In the management of hypertension, the compounds of this invention may be utilized in compositions such as tablets, capsules or elixers for oral administration, suppositories for rectal administration, sterile solutions or suspensions for parenteral or intramuscular administration, and the like. The compounds of this invention can be administered to patients (animals and human) in need of such treatment in dosages that will provide optimal pharmaceutical efficacy. Although the dose will vary from patient to patient depending upon the nature and severity of disease, the patient's weight, special diets then being followed by a patient, concurrent medication, and other factors which those skilled in the art will recognize, the dosage range will generally be about 10 to 100 mg per kilogram of patient body weight per day, which can be administered in single or multiple doses. Naturally, these dose ranges can be adjusted on a unit basis as necessary to permit divided daily dosage and, as noted above, the dose will vary depending on the nature and severity of the disease, weight of patient, special diets and other factors.

Typically, these combinations can be formulated into pharmaceutical compositions according to standard procedures generally known in the art.

About 1 to 100 mg of a compound or mixture of compounds of formula I or a physiologically acceptable salt is compounded with a physiologically acceptable vehicle carrier, excipient, binder, preservative, stabilizer, flavor, etc., in a unit dosage form as called for by accepted pharmaceutical practice. The amount of active substance in these compositions or preparations is such that a suitable dosage in the range indicated is obtained.

Illustrative of the adjuvants which may be incorporated in tablets, capsules and the like are the following: a binder such as gum tragacanth, acacia, corn starch or gelatin; an excipient such as microcrystalline cellulose; a disintegrating agent such as corn starch, pregelatinized starch, alginic acid and the like; a lubricant such as magnesium stearate; a sweetening agent such as sucrose, lactose or saccharin; a flavoring agent such as peppermint, oil of wintergreen or cherry. When the dosage unit form is a capsule, it may contain in addition to materials of the above type, a liquid carrier such as fatty oil. Various other materials may be present as coatings or to otherwise modify the physical form of the dosage unit. For instance, tablets may be coated with shellac, sugar or both. A syrup or elixir may contain the active compound, sucrose as a sweetening agent, methyl and propyl parabens as preservatives, a dye and a flavoring such as cherry or orange flavor.

Sterile compositions for injection can be formulated according to conventional pharmaceutical practice by dissolving or suspending the active substance in a vehicle such as water for injection, a naturally occurring vegetable oil like sesame oil, coconut oil, peanut oil, cottonseed oil, etc., or a synthetic fatty vehicle like ethyl oleate or the like. Buffers, preservatives, antioxidants and the like can be incorporated as required.

What is claimed is:

1. A compound of the formula

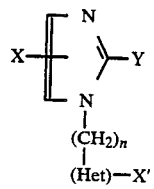

wherein n is zero or 1-4; X is hydrogen, $C_{1-6}$ lower alkyl, chloro, bromo, phenyl, benzyl, or Z-substituted phenyl or benzyl with Z being $C_{1-6}$ lower alkyl or halogen; Y is —$CH_2NR_1R_2$, —$CONH_2$, —$COCOOR_1$, —$CSNH_2$ or —$C(=NH)NR_1R_2$; $R_1$ and $R_2$ independently represent hydrogen or $C_{1-6}$ lower alkyl; Het is a heterocycle of the group consisting of thienyl, furyl, pyridinyl, pyrazolyl, pyrimidinyl, pyrrolyl, thiazolyl and imidazol-2-yl; and X' is hydrogen, halogen or a $C_{1-6}$ lower alkyl; and the non-toxic pharmaceutically acceptable salts thereof.

2. A compound according to claim 1 which has the formula:

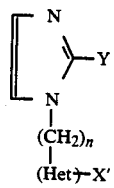

wherein n is zero or 1-4; Y is —$CH_2NR_1R_2$, —$CONH_2$, —$COCOOR_1$, —$CSNH_2$ or —$C(=NH)NR_1R_2$; $R_1$ and $R_2$ independently represent hydrogen or $C_{1-6}$ lower alkyl; Het is a heterocycle of the group consisting of thienyl, furyl, pyridinyl, pyrazolyl, pyrimidinyl, pyrrolyl, thiazolyl and imidazol-2-yl; and X' is hydrogen, halogen or a $C_{1-6}$ lower alkyl; and the non-toxic pharmaceutically acceptable salts thereof.

3. A compound according to claim 1 which has the formula:

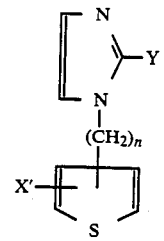

wherein n is zero or 1-4; Y Is —$CH_2NR_1R_2$, —$CONH_2$, —$COCOOR_1$, —$CSNH_2$ or —$C(=NH)NR_1R_2$; $R_1$ and $R_2$ independently represent hydrogen or $C_{1-6}$ lower alkyl; and X' is hydrogen, halogen or a $C_{1-6}$ lower alkyl; and the non-toxic pharmaceutically acceptable salts thereof.

4. A compound according to claim 1 which has the formula:

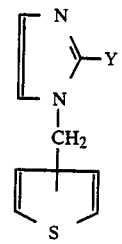

wherein Y is —$CH_2NR_2'R_2$, —$CONH_2$, —$COCOOR_1$, —$CSNH_2$ or —$C(=NH)NR_1R_2$; $R_1$ and $R_2$ independently represent hyrdrogen or $C_{1-6}$ lower alkyl; and the non-toxic pharmaceutically acceptable salts thereof.

5. A compound according to claim 1 which is 1-(2-thienylmethyl)-2-thiocarbamyl-1H-imidazole.

6. A compound according to claim 1 which is 1-(2-thienylmethyl)-2-carbamyl-1H-imidazole.

7. A compound according to claim 1 which is 2-aminomethyl-1-(2-thienylmethyl)-1H-imidazole.

8. A compound according to claim 1 which is 1-(2-thienylmethyl)-1H-imidazole-2-carboximidamide.

9. A compound according to claim 1 which is methyl α-oxo-1-(2-thienylmethyl)-1H-imidazole-2-acetate.

* * * * *

UNITED STATES PATENT AND TRADEMARK OFFICE
CERTIFICATE OF CORRECTION

PATENT NO. : 4,810,800
DATED : March 7, 1989
INVENTOR(S) : Donald P. Matthews et al.

It is certified that error appears in the above-identified patent and that said Letters Patent is hereby corrected as shown below:

Column 6, Line 20 patent reads: "10.0g" and should read --10.9g--.

Column 11, Line 13 patent reads: "betwen" and should read --between--.

Column 13, Line 29 patent reads: "blask" and should read --flask--.

Column 14, Line 38 patent reads: "152'-154°C" and should read --152-154°C--.

Column 14, Line 55 patent reads: "1H-imidazle" and should read --1H-imidazole--.

Column 14, Line 56 patent reads: "at above" and should read --at about--.

Column 18, Line 40 patent reads: "-$CH_2NR_{2'R_2}$," and should read ---$CH_2NR_1R_2$,--.

Signed and Sealed this

Twelfth Day of November, 1991

Attest:

HARRY F. MANBECK, JR.

*Attesting Officer*     *Commissioner of Patents and Trademarks*